United States Patent [19]

Regel et al.

[11] 4,301,166
[45] Nov. 17, 1981

[54] HYDROXYETHYL-AZOLE COMPOUNDS, THEIR PRODUCTION AND THEIR MEDICINAL USE

[75] Inventors: Erik Regel; Karl H. Büchel; Ingo Haller; Manfred Plempel, all of Wuppertal, Fed. Rep. of Germany

[73] Assignee: Bayer Aktiengesellschaft, Leverkusen, Fed. Rep. of Germany

[21] Appl. No.: 92,806

[22] Filed: Nov. 9, 1979

[30] Foreign Application Priority Data

Nov. 25, 1978 [DE] Fed. Rep. of Germany ....... 2851116

[51] Int. Cl.³ .................... A01N 43/50; A01N 43/82; C07D 233/60; C07D 249/08
[52] U.S. Cl. .............................. 424/269; 260/665 G; 424/232; 424/273 R; 548/262; 548/341; 568/327; 568/328; 568/329; 568/330; 568/331; 568/335; 568/337; 568/807; 568/808; 568/809

[58] Field of Search ................ 548/262, 341; 424/269, 424/273 R, 232

[56] References Cited

U.S. PATENT DOCUMENTS 4,113,465  9/1978  Shephard et al. ................... 424/269

FOREIGN PATENT DOCUMENTS 2623129 11/1977 Fed. Rep. of Germany ...... 548/341
1464224  2/1977 United Kingdom ................ 548/262

Primary Examiner—Alton D. Rollins
Attorney, Agent, or Firm—Sprung, Felfe, Horn, Lynch & Kramer

[57] ABSTRACT

The invention relates to hydroxyethyl-azole compounds and methods for their preparation. Also included in the invention are compositions containing said hydroxyethyl-azole compounds and methods for the use of said compounds and compositions as antimycotic agents.

11 Claims, No Drawings

HYDROXYETHYL-AZOLE COMPOUNDS, THEIR PRODUCTION AND THEIR MEDICINAL USE

The present invention relates to certain new hydroxyethyl-azole compounds to processes for their production and to their use as antimycotic agents It has already been disclosed that 1-(β-aryl)-ethylimidazole derivatives, such as, in particular, 1-[2,4-dichloro-β-(2,4-dichlorobenzyloxy)-phenethyl]-imidazole nitrate, have a good antimycotic action (compare DE-AS (German Published Specification No.) 1,940,388) However, their in vivo action is not always satisfactory, especially against Candida.

According to the present invention there are provided compounds which are hydroxyethyl-azoles of the general formula

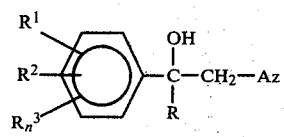 (I)

or a salt thereof
in which

Az denotes an imidazole or triazole radical

R denotes an optionally substituted phenyl, naphthyl or tetrahydronaphthyl radical;

$R^1$ denotes an optionally substituted phenyl or cycloalkyl radical, $R^2$ denotes a hydrogen atom, or $R^1$ and $R^2$ together, in the o-position relative to one another, denote an optionally substituted methylene bridge with several members, or, together with the phenyl ring, complete a naphthyl radical, $R^3$ denotes a halogen atom or an alkyl, alkoxy or halogeno-alkyl group and n is 0, 1, 2 or 3.

The compounds of the present invention have powerful antimycotic properties.

According to the present invention there is further provided a process for the production of compounds of the present invention in which (a) an azolylmethyl phenyl ketone of the general formula

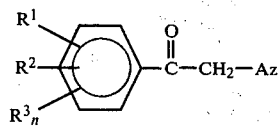 (II)

in which

Az, $R^1$, $R^2$, $R^3$ and n have the meaning indicated above, is reacted with a Grignard compound of the general formula

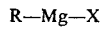 R—Mg—X (III)

in which

R has the meaning indicated above and

X denotes a halogen atom, preferably a chlorine or bromine atom, in the presence of a diluent, or (b) a 1-halogeno-ethan-2-ol of the general formula

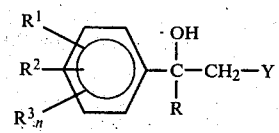 (IV)

in which

R, $R^1$, $R^2$, $R^3$ and n have the meaning indicated above and

Y denotes a halogen atom, preferably a chlorine or bromine atom, is reacted with an azole of the general formula

 Z—Az (V)

in which

Az has the meaning indicated above and

Z denotes a hydrogen atom or an alkali metal, preferably in the presence of an acid-binding agent and preferably in the presence of a diluent; and the product of reaction variant (a) or (b) is, if desired, converted into a salt by reaction with an acid.

The hydroxyethylazoles of the formula (I) obtainable according to the invention can also be converted into salts by reaction with acids. Among the new hydroxyethylazole salts of the invention, those salts that are pharmaceutically acceptably are particularly important and are preferred.

Surprisingly, the hydroxyethyl-azoles according to the invention exhibit, in addition to a good antimycotic in vitro activity, a better, therapeutically usable in vivo activity against Candida than 1-[2,4-dichloro-β-(2,4-dichlorobenzyloxy)-phenethyl]-imidazole nitrate, which is known and is recognised as a good agent of the same type of action. The active compounds according to the invention thus represent a valuable advance in pharmacy.

Preferred hydroxyethyl-azoles of the present invention are those in which Az denotes an imidazol-1-yl, 1,2,4-triazol-1-yl or 1,3,4-triazol-1-yl radical, R denotes an optionally substituted phenyl, naphthyl or tetrahydronaphthyl radical, preferred substituents being: halogen, preferably fluorine, chlorine and bromine, straight-chain or branched alkyl and alkoxy with in each case 1 to 4 carbon atoms, and halogenalkyl with 1 to 4 carbon atoms and up to 5 halogen atoms, preferably with 1 or 2 carbon atoms and up to 3 identical or different halogen atoms, halogens being, preferably fluorine and chlorine, and trifluoromethyl being mentioned as an example; $R^1$ denotes an optionally substituted phenyl or $C_3$ to $C_7$ cycloalkyl radical, preferred substituents being: halogen, preferably fluorine, chlorine or bromine, and alkyl with 1 to 4, preferably with 1 to 5, carbon atoms and $R^2$ denotes a hydrogen atom, or $R^1$ and $R^2$ together, in the ortho-position relative to one another, denote a methylene bridge which has 3 to 5 methylene groups and is optionally monosubstituted or polysubstituted, preferred substituents which may be mentioned being: halogen, preferably fluorine, chlorine or bromine, and alkyl with 1 to 4, preferably with 1 to 2, carbon atoms, or $R^1$ and $R^2$, together with the phenyl ring, complete a naphthyl radical; $R^3$ denotes a halogen atom, preferably fluorine, chlorine or bromine, a straight-chain or branched alkyl or alkoxy group with in each case 1 to 4 carbon atoms, or a halogenoalkyl group with 1 to 4 atoms and up to 5 halogen atoms, preferably with 1 or 2 carbon atoms, and up to 3 identical or different halogen atoms, halogens being, preferably, fluorine and chlorine and trifluoromethyl being mentioned as an example; and n is 0, 1 or 2.

Very particularly preferred compound of the present invention are those in which Az denotes a imidazol-1-yl or 1,2,4-triazol-1-yl radical, R¹ denotes a phenyl radical, which is optionally monosubstituted or disubstituted by chlorine, fluorine or methyl, or denotes a naphthyl or tetrahydronaphthyl radical; R¹ denotes a phenyl, cyclopentyl or cyclohexyl radical, which is optionally monosubstituted or disubstituted by chlorine, bromine, fluorine or methyl, and R² denotes a hydrogen atom, or R¹ and R² together, in the ortho-position relative to one another, denote a trimethylene, tetramethylene or pentamethylene bridge, which is optionally substituted by chlorine or methyl, or, together with the phenyl ring, complete a naphthyl radical; R³ denotes a chlorine or fluorine atom or a methyl group; and n is 0 or 1.

The following compounds of the general formula (I) can be mentioned specifically as included in the invention, in addition to the compounds mentioned in the preparation examples:

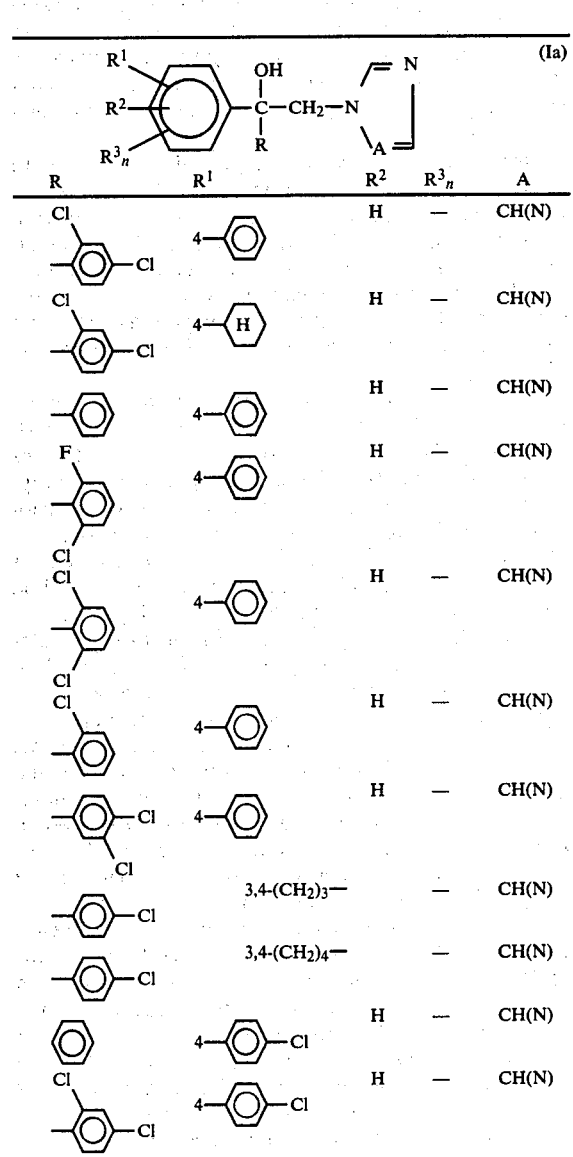

If, for example, 4-biphenyl imidazol-1-yl-methyl ketone and 4-chlorophenyl-magnesium chloride are used as starting materials, the course of the reaction can be represented by the following equation (process variant a)

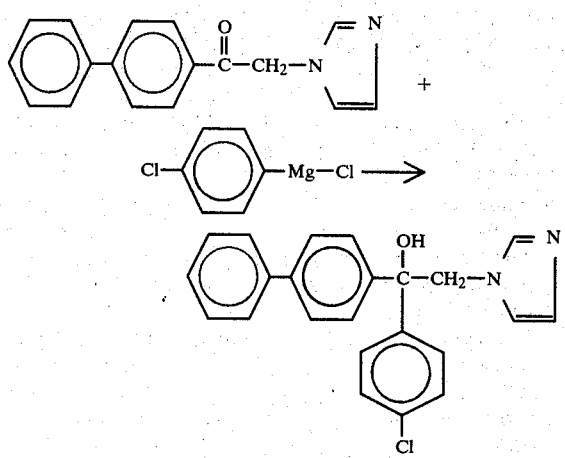

If 1-(4-biphenyl)-1-(2,4-dichlorophenyl)-2-chloroethanol and sodium imidazole are used as starting materials the course of the reaction can be represented by the following equation (process variant b):

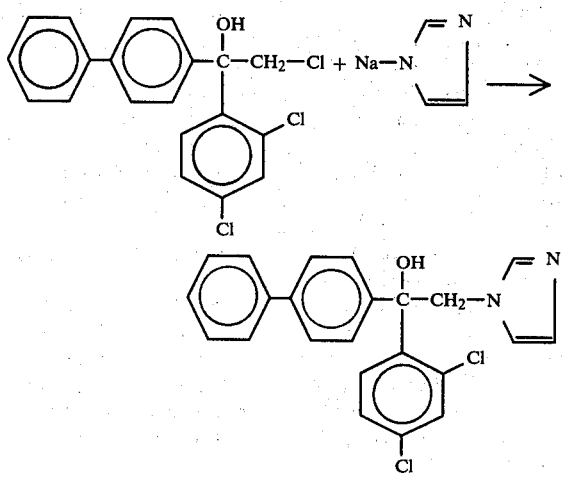

Preferred compounds of formula (II) to be used as starting materials for process variant (a) are those in which Az, $R^1$, $R^2$, $R^3$ and n have the meaning indicated for the mentioned preferred and very particularly preferred hydroxyethyl-azoles of the invention.

The azolylmethyl phenyl ketones of the formula (II) are novel. However, they can be prepared in known manner by reacting corresponding phenacyl halides of the formula

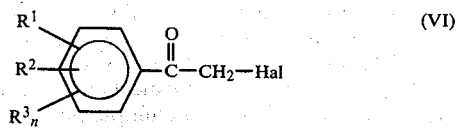

(VI)

in which $R^1$, $R^2$, $R^3$ and n have the meaning indicated above and

Hal denotes a chlorine or bromine atom, with azoles in the presence of a diluent, such as, for example, di-methylformamide, and in the presence of an acidbinding agent, such as, in particular, an excess of azole, at temperatures between 20° and 80° C. (in this context, compare also the statements in U.S. Pat. No. 3,658,813).

Examples of the starting substances of the formula (II) which may be mentioned are: 4-biphenyl imidazol-1-yl-methyl ketone, 4-(4'-chlorophenylyl) imidazol-1-yl-methyl ketone, 2-biphenyl imidazol-1-yl-methyl ketone, 4-(2',4'-dichlorobiphenylyl) imidazol-1-yl-methyl ketone, 2-chloro-4-biphenyl imidazol-1-yl-methyl ketone, 2-chloro-4-(4'-chlorobiphenyl) imidazol-1-yl-methyl ketone, 4-cyclohexylphenyl imidazol-1-yl-methyl ketone, 4-cyclopentylphenyl imidazol-1-yl-methyl ketone, 4-chloro-3-cyclohexylphenyl imidazol-1-yl-methyl ketone, 4-(3-bromocyclohexyl)phenyl imidazol-1-yl-methyl ketone, 4-cyclopentyl-2-chlorophenyl imidazol-1-yl-methyl ketone, 4-cyclopentyl-2-fluorophenyl imidazol-1-yl-methyl ketone, 4-cyclopentyl-2-methyl-phenyl imidazol-1-yl-methyl ketone, 4-(1-methylcyclohexyl)-phenyl imidazol-1-yl-methyl ketone, 4-cycloheptylphenylimidazol-1-yl-methyl ketone, 4-cycloheptyl-2-chlorophenyl imidazol-1-yl-methyl ketone, naphth-1-yl imidazol-1-yl-methyl ketone, naphth-2-yl imidazol-1-yl-methyl ketone, 1,2,3,4-tetrahydro-naphth-5-yl imidazol-1-yl-methyl ketone, 1,2,3,4-tetrahydro-naphth-6-yl imidazol-1-yl-methyl ketone, and indan-4-yl imidazol-1-yl-methyl ketone, and the corresponding 1,2,4-triazol-1-yl ketones and 1,3,4-triazol-1-yl ketones.

Preferred Grignard compounds of formula (III) to be used as starting materials for process variant (a) are those in which R has the meaning indicated for the mentioned preferred and very particularly preferred hydroxyethylazoles of the invention.

The Grignard compounds of the formula (III) are generally known compounds of organic chemistry. Examples which may be mentioned are: phenyl-magnesium chloride, 4-chlorophenyl-magnesium chloride, 2,4-dichlorophenyl-magnesium chloride, 2,6-dichlorophenyl-magnesium chloride, 2-chloro-6-fluorophenyl-magnesium chloride, 2-chlorophenylmagnesium chloride, 3-chlorophenyl-magnesium chloride, 3,4-dichlorophenyl-magnesium chloride, naphth-2-yl-magnesium chloride and 1,2,3,4-tetrahydronaphth-6-yl-magnesium chloride, and the corresponding bromides.

Although not specifically named, herein in order to avoid a prolix presentation, this disclosure is intended to include each of the specific compounds of the invention resulting when a specific starting substance of the formula (II) as enumerated above is reacted with a specific Grignard compound of the formula (III) as enumerated above.

Preferred 1-halogeno-ethan-2-ols to be used as starting materials for process variant (b) are those in which R, $R^1$, $R^2$, $R^3$ and n have the meanings indicated for the mentioned preferred and very particularly preferred hydroxyethyl-azoles of the invention.

The 1-halogeno-2-ols of the formula (IV) are novel. However, they can be prepared in known manner, by reacting ketones of the formula (VI) with Grignard compounds of the formula (III) according to process variant (a) (in this comtext, compare also the statements in DE-OS (German Published No.) 2,623,129 and the preparation examples).

Preferred azoles of formula (V) to be used as starting materials for process variant (b) are those in which Az has the meaning indicated for the mentioned preferred and very particularly preferred hydroxyethyl-azoles of the invention, and Z preferably denotes a hydrogen atom or sodium.

The azoles of the formula (V) are generally known compounds of organic chemistry.

All the solvents customary for a Grignard reaction can be used as the diluent for the reaction, according to the invention, in process variant (a). Preferred solvents include ethers, such as diethyl ether or tetrahydrofurane, and mixtures with other organic solvents, such as, for example, benzene.

The reaction temperatures can be varied within a substantial range in process variant (a). The reaction is preferably carried out between 20° and 120° C., more preferably between 30° and 80° C.

An excess of the Grignard compound of the formula (III) of 3 to 5 mols is preferably used per 1 mol of the compound of the formula (II) in carrying out process (a). Isolation of the compounds of the formula (I) is effected in known manner.

Preferred possible diluents for the reaction, according to the invention, in process variant (b) are inert organic solvents. Preferred solvents include ketones, such as diethyl ketone, and in particular acetone and methyl ethyl ketone; nitriles, such as propionitrile, and in particular acetonitrile; alcohols (particularly alkanols having 1 to 3 carbon atoms) such as ethanol or isopropanol; ethers, such as tetrahydrofurane or dioxane; aromatic hydrocarbons, such as benzene, toluene and dichlorobenzene; formamides, such as, in particular, dimethylformamide and diethylformamide, and halogenated hydrocarbons (particularly chlorinated alkanes), such as methyl chloride, carbon tetrachloride or chloroform.

If process variant (b) according to the invention is carried out in the presence of an acid-binding agent, it is possible to add any of the inorganic or organic acid-binding agents which can usually be employed, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylmethylamine or N,N-dimethylbenzylamine, and furthermore pyridine and diazabicyclooctane. An excess of azole is preferably used.

The reaction temperatures can be varied within a substantial range in process variant (b). The reaction is preferably carried out between 30° and 200° C. at the boiling point of the solvent.

1 to 2.5 mols of azole and 1 to 2.5 mols of acidbinding agent are preferably employed per 1 mol of the compounds of the formula (IV) in carrying out process variant (b) according to the invention. If an alkali metal salt is used, 1 to 1.5 mols thereof are preferably employed per 1 mol of the compound of the formula (IV). To isolate the compounds of the formula (I), the solvent is distilled off and the residue is washed with water directly or after being taken up in an organic solvent, in which case the organic phase is dried over sodium sulphate and freed from solvent in vacuo. The residue is appropriately purified by distillation or recrystallisation or by chromatography.

All the acids which give rise to pharmaceutically acceptable salts can be used for such salt preparation. These acids include, preferably, hydrogen halide acids, such as for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The salts of the compounds of the formula (I) can be obtained in a simple manner by the usual methods of salt formation, for example by dissolving a compound of the formula (I) in a suitable inert solvent and adding the acid, for example hydrochloric acid, and they can be isolated in a known manner, for example, by filtration, and if appropriate purified by washing with an inert organic solvent.

The compounds of the present invention display an antimicrobial action, in particular an antimycotic action. They possess a very broad antimycotic action spectrum, especially against dermatophytes and blastomyces as well as biphase fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as Trichophyton mentagrophytes, varieties of Microsporon, such as *Microsporon felineum* and varieties of Penicillium, such as *Penicillium commune*. This list of microorganisms can in no way implies a limitation of the germs which can be combated but is only illustrative.

Examples which may be mentioned of fields of application in medicine are: dermatomycoses and systemic mycoses caused by *Trichophyton mentagrophytes* and other varieties of Trichophyton, varieties of Microsporon, Epidermophyton Floccosum, balstomyces and biphase fungi as well as moulds.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fourth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (9b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams, and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in reaction to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition in the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer amounts of from 10 mg to 300 mg/kg, preferably 50 mg to 200 mg/kg, of body weight per day to achieve effective results. Nevertheless, it can at times be necessary to deviate from those dosage rates, and in particular to do so as a function of the nature and body weight of the animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples A, B and C illustrate the in vitro and in vivo activity of compounds of the present invention.

EXAMPLE A

Antimycotic in vitro activity

Description of the experiment

The in vitro tests were carried out in a series dilution test with germ inocula of an average of $5 \times 10^4$ germs/ml of substrate. The nutrient medium was (a) for dermatophytes and moulds: Sabouraud's milieu d'epreuve and (b) for yeasts: meat extract/glucose broth.

The incubation temperature was 27° C. and the duration of incubation was 24 to 96 hours.

In these tests, the compounds according to the invention showed very good minimum inhibitory concentrations.

EXAMPLE B

Antimicrobial in vivo activity (oral) in candidosis of mice

Description of the experiment

Mice of the SPF-CF$_1$ type were infected intravenously with $1-2 \times 10^6$ logarithmically growing Candida cells, which were suspended in physiological sodium chloride solution. The animals are treated orally one hour before and seven hours after the infection, with, in each case, 50–100 mg/kg of body weight of the formulations.

Result

Untreated animals died 3 to 6 days after infection. The survival rate on the 6th day after infection was about 5% in the case of untreated control animals.

In this test, the compounds according to the invention showed an action, which in some cases was very good (60 to $\geq$90% of survivors on the 6th day after infection), whilst "Miconazol" showed no action at these dosages.

It should be pointed out in particular, that some of the compounds according to the invention are also effective in the case of oral therapy of aspergillosis of mice.

EXAMPLE C

Antimycotic in vivo activity (local) using experimental trichophytosis of guinea pigs as an example Description of the experiment White guinea pigs of the Pirbright-white strain were infected with a microconidia and macroconidia suspension of Trichophyton mentagrophytes of their shaven, non-scarified backs. The typical pattern of dermatophytosis with reddening, scaling and loss of hair up to total integumentary defect at the point of infection developed on the untreated animals within 12 days after infection. The infected animals were treated locally once daily, starting on the 3rd day after infection, with 1% strength solutions of the formulations according to the invention in polyethylene glycol.

On the 14th day after infection, the untreated control animals exhibited the typical pattern of dermatophytosis, whilst preparation examples 1, 2, 4, 8 and 10, for example, had partly to completely inhibited the course of the infection.

The following Examples illustrate the production of compounds of the present invention.

EXAMPLE 1

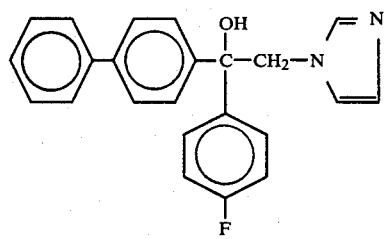

(Process b)

20.2 g (0.297 mol) of imidazole are added to a solution of 9.5 g (0.175 mol) of sodium methylate in 49 ml of methyl alcohol. A slution of 44.3 g (0.135 mol) of 1-(4-biphenylyl)-2-chloro-1-(4-fluorophenyl)-ethanol in 103 mol of dimethylformamide is then added dropwise, and the reaction mixture is heated to 60° C. for 90 minutes. It is concentrated by distilling off the solvent in vacuo, and the residue is stirred with water. The crystals which remain are washed with acetonitrile and recrystallised from ethyl alcohol. 13.5 g (28% of theory) of 1-(4-biphenylyl)-1-(4-fluorophenyl)-2-(imidazol-1-yl)-ethanol of melting point 220° C. are obtained.

Preparation of the starting material

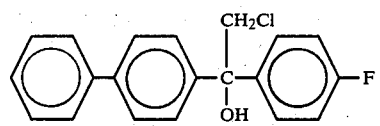

34.5 g (0.15 mol) of 4-phenylphenacyl chloride are added in portions to a solution of 4-fluorophenyl-magnesium bromide, obtained from 7.3 g (0.33 mol) of magnesium and 52.5 g (0.3 mol) of 4-fluorobromobenzene in 100 ml of diethyl ether. After heating the reaction mixture under reflux for two hours, it is poured onto aqueous ammonium chloride solution. The ether phase is separated off, washed with water, dried over sodium sulphate and evaporated. 44.3 g of 1-(4-biphenylyl)-2-chloro-1-(4-fluorophenyl)-ethanol are obtained.

EXAMPLE 2

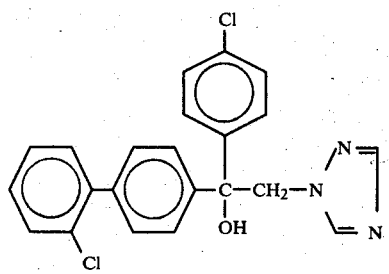

(Process b)

Analogously to Example 1, 16.2 g (40% of theory) of 1-(2'-chloro-4-biphenylyl)-1-(4-chlorophenyl)-2-(1,2,4-triazol-1-yl)-ethanol of melting point 190° C. are obtained from 7.02 g (0.13 mol) of sodium methylate, 14.96 g (0.22 mol) of triazole, 40 g (0.1 mol) of 1-(2'-chloro-4-biphenylyl)-2-chloro-1-(4-chlorophenyl)-ethanol, 36 ml of methyl alcohol and 75 ml of dimethylformamide, after heating the mixture to 70° C. for 3 hours.

Preparation of the starting material

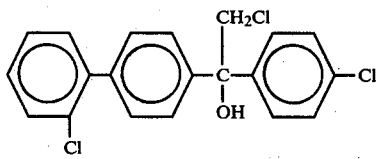

Analogously to Example 1, 75 g of 1-(2'-chloro-4-biphenylyl)-2-chloro-1-(4-chlorophenyl)-ethanol are obtained from 10.69 g (0.44 mol) of magnesium, 76.6 g (0.4 mol) of 4-bromochlorobenzene and 53 g (0.2 mol) of 4-(2-chlorophenyl)-phenacyl chloride.

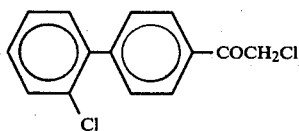

293.7 g (2.2 mols) of aluminium chloride are introduced in portions to a solution of 377 g (2 mols) of 2-chlorobiphenyl in 160 ml (2 mols) of chloroacetyl chloride and 1,000 ml of methylene chloride. After 18 hours, the reaction mixture is poured onto ice and hydrochloric acid. The organic phase is seperated off, washed, dried over sodium sulphate and concentrated in vacuo by distilling off the solvent. The oil which remains is purified by distillation. 478.7 g (90% of theory) of 4(2-chlorophenyl)phenacyl chloride of melting point 47° C. are obtained.

EXAMPLE 3

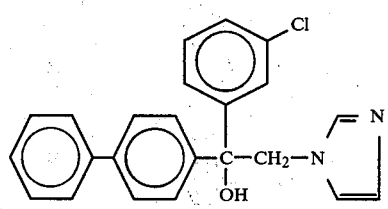

(Process a)

13.1 g (0.05 mol) of 4-biphenylyl imidazol-1-ylmethyl ketone are added in portions to 21.6 g (0.1 mol) of 3-chlorophenyl-magnesium bromide (prepared from 2.4 g (0.1 mol) of magnesium and 19.1 g (0.1 mol) of 3-bromochlorobenzene) in 70 ml of ether. After adding 500 ml of dry toluene, the ether is distilled off and the suspension formed is treated with aqueous ammonium chloride solution. The toluene phase is separated off and filtered and the filtrate is dried over sodium sulphate. It is concentrated by distilling off the toluene in vacuo, and the crystalline residue is stirred with acetonitrile. After recrystallising the residue from ethanol, 9.4 g (50% of theory) of 1-(4-biphenylyl)-1-(3-chlorophenyl)-2-(imidazol-1-yl)-ethanol of melting point 202° C. are obtained.

The compounds in Table 1 below are obtained in a corresponding manner, either by process (a) or by process (b).

TABLE 1

| Example No. | R | $R^1$ | $R^2$ | $R^3_n$ | Az | Melting point (°C.) |
|---|---|---|---|---|---|---|
| 4 | —⌬—Cl | Cl, 4—⌬ | H | — | —N⟨N= | 187 |
| 5 | Cl, ⌬ | Cl, 4—⌬ | H | — | —N⟨N= | 206 |
| 6 | Cl, ⌬ | Cl, 4—⌬—Cl | H | — | —N⟨N= | 220 |

TABLE 1-continued

Structure: Phenyl ring with substituents R¹, R², R³ₙ, and a side chain —C(OH)(R)—CH₂—Az

| Example No. | R | R¹ | R² | R³ₙ | Az | Melting point (°C.) |
|---|---|---|---|---|---|---|
| 7 | 4-Cl-C₆H₄— | 4-Cl (2,4-diCl-C₆H₃) | H | — | imidazol-1-yl | 176 |
| 8 | 4-F-C₆H₄— | 4-Cl (2,4-diCl-C₆H₃) | H | — | imidazol-1-yl | 100 |
| 9 | 4-F-C₆H₄— | 4-Cl (2,4-diCl-C₆H₃) | H | — | imidazol-1-yl | 225 |
| 10 | 4-Cl-C₆H₄— | 4-C₆H₅ | H | — | imidazol-1-yl | 230 |
| 11 | 4-Cl-C₆H₄— | 4-(4-Cl-C₆H₄) | H | — | imidazol-1-yl | 188 |
| 12 | 4-F-C₆H₄— | 4-(4-Cl-C₆H₄) | H | — | imidazol-1-yl | 218 |
| 13 | 2-Cl-C₆H₄— | 4-(4-Cl-C₆H₄) | H | — | imidazol-1-yl | 206 |
| 14 | 4-Cl-C₆H₄— | 4-(4-Cl-C₆H₄) | H | — | 1,2,4-triazol-1-yl | 189 |
| 15 | 4-F-C₆H₄— | 4-(4-Cl-C₆H₄) | H | — | 1,2,4-triazol-1-yl | 217 |
| 16 | 2-Cl-C₆H₄— | 4-(4-Cl-C₆H₄) | H | — | 1,2,4-triazol-1-yl | 144 |
| 17 | C₆H₅— | 4-C₆H₅ | H | — | imidazol-1-yl | 224 |
| 18 | 2-Cl-C₆H₄— | 4-C₆H₅ | H | — | imidazol-1-yl | 222 |
| 19 | 2-F-C₆H₄— | 4-C₆H₅ | H | — | imidazol-1-yl | 202 |
| 20 | 2-F-C₆H₄— | 4-(4-CH₃-C₆H₄) | H | — | imidazol-1-yl | 200 |
| 21 | 2-F-C₆H₄— | 4-C₆H₅ | H | — | 1,2,4-triazol-1-yl | 164 |
| 22 | 2-F-C₆H₄— | 4-C₆H₅ | H | — | 1,2,4-triazol-4-yl | 170 |
| 23 | 2-Cl-C₆H₄— | 4-(2-Cl-C₆H₄) | H | — | imidazol-1-yl | 206 |

TABLE 1-continued

| Example No. | R | R¹ | R² | R³ₙ | Az | Melting point (°C.) |
|---|---|---|---|---|---|---|
| 24 | F, phenyl | 4-Cl-phenyl | H | — | 1,2,4-triazol-1-yl | 227 |
| 25 | Cl, phenyl | 4-CH₃-phenyl | H | — | 1,2,4-triazol-1-yl |  |
| 26 | Cl, phenyl | 4-OCH₃-phenyl | H | — | 1,2,4-triazol-1-yl |  |
| 27 | 4-Cl-phenyl | 4-C(CH₃)₃-phenyl | H | — | 1,2,4-triazol-1-yl |  |
| 28 | Cl, phenyl | 4-phenyl | H | — | 1,2,4-triazol-1-yl | 160 |
| 29 | Cl, phenyl | 4-phenyl | H | — | 1,2,4-triazol-4-yl | 220 |

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the animal's body to the active compound.

What is claimed is:

1. A hydroxyethyl-azole of the formula

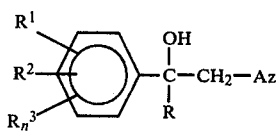

or a salt thereof
in which
  Az represents imidazol-1-yl, 1,2,4-triazol-1-yl or 1,2,4-triazol-4-yl,
  R denotes optionally substituted phenyl, naphthyl or tetrahydronaphthyl which is unsubstituted or substituted by halogen, C₁-C₄-alkyl, C₁-C₄-alkoxy or halogenoalkyl with 1 to 4 carbon atoms and up to 5 halogen atoms,
  R¹ represents phenyl which is unsubstituted or substituted by halogen or C₁-C₄-alkyl and
  R² represents hydrogen, or
  R¹ and R² together, in the o-position relative to one another, represent an optionally halogen or C₁-C₄-alkyl substituted methylene bridge with 3 to 5 methylene groups, or, together with the phenyl ring, represent naphthyl,
  R³ represents halogen, an alkyl, or alkoxy group with in each case 1 to 4 carbon atoms or halogenoalkyl with 1 to 4 carbon atoms and up to 5 halogen atoms and
  n is 0, 1, 2 or 3.

2. A compound according to claim 1 in which Az denotes an imidazol-1-yl, 1,2,4-triazol-1-yl or 1,3,4-triazole-1-yl radical, R denotes an optionally substituted phenyl, naphthyl or tetrahydronaphthyl radical which is unsubstituted or substituted by halogen, C₁-C₄-alkyl, C₁-C₄-alkoxy or halogenoalkyl, with 1 to 4 carbon atoms and up to 5 halogen atoms, R¹ denotes an optionally substituted phenyl and R² denotes a hydrogen atom, or R¹ and R² together, in the ortho-position relative to one another, denote a methylene bridge which has 3 to 5 methylene groups and is optionally monosubstituted or polysubstituted by halogen or C₁-C₄-alkyl, or R¹ and R², together with the phenyl ring, complete a naphthyl radical; R³ denotes a halogen atom, a straight-chain or branched alkyl or alkoxy group with in each case 1 to 4 carbon atoms, or a halogenoalkyl group with 1 to 4 carbon atoms and up to 5 halogen atoms, and n is 0, 1 or 2.

3. A compound according to claim 1 in which Az denotes an imidazol -1-yl or 1,2,4-triazol-1-yl radical, R denotes a phenyl radical, which is optionally monosubstituted or disubstituted by chlorine, fluorine or methyl, or denotes a naphthyl or tetrahydronaphthyl radical, R¹ denotes a phenyl radical, which is optionally monosubstituted or disubstituted by chlorine, bromine, fluorine or methyl, and R² denotes a hydrogen atom, or R¹ and R² together, in the ortho-position relative to one another, denote a trimethylene, tetramethylene or pentamethylene bridge, which is optionally substituted by chlorine or methyl, or, together with the phenyl ring, complete a naphthyl radical, R³ denotes a chlorine or fluorine atom or a methyl group, and n is 0 or 1.

4. A pharmaceutical composition containing as an active ingredient an antimycotically effective amount of a compound according to claim 1 in admixture with a diluent.

5. A pharmaceutical composition of claim 4 in the form of a sterile or physiologically isotonic aqueous solution.

6. A composition according to claim 4 or 5 containing from 0.5 to 95% by weight of the said active ingredient.

7. A medicament in dosage unit form comprising an antimycotically effective amount of a compound according to claim 1 together with an inert pharmaceutical carrier.

8. A medicament of claim 7 in the form of tablets, pills, dragees, capsules, ampoules or suppositories.

9. A method of combating mycoses in warm-blooded animals which comprises administering to the animals an antimycotically effective amount of an active compound according to claim 1 either alone or in admixture with a diluent or in the form of a medicament.

10. A method according to claim 9 in which the active compound is administered in an amount of 50 to 200 mg per kg body weight per day.

11. A method according to claim 9 or 10 in which the active compound is administered parenterally.

* * * * *